United States Patent [19]

Baeck et al.

[11] Patent Number: 6,077,818

[45] Date of Patent: *Jun. 20, 2000

[54] CELLULASE ACTIVITY CONTROL BY A TERMINATOR

[75] Inventors: Andre Cesar Baeck, Bonheiden; Alfred Busch, Londerzeel, both of Belgium; Andre Christian Convents, Cincinnati, Ohio; Olivier Paquatte, Strombeek-Bever, Belgium

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 09/125,580

[22] PCT Filed: Feb. 18, 1997

[86] PCT No.: PCT/US97/02515

§ 371 Date: Oct. 13, 1998

§ 102(e) Date: Oct. 13, 1998

[87] PCT Pub. No.: WO97/30143

PCT Pub. Date: Aug. 21, 1997

[30] Foreign Application Priority Data

Feb. 20, 1996 [EP] European Pat. Off. .............. 96870013

[51] Int. Cl.[7] ........................... C11D 3/386; C11D 3/395; C11D 3/16; C11D 3/280

[52] U.S. Cl. ................. 510/374; 510/302; 510/305; 510/306; 510/309; 510/320; 510/321; 510/336; 510/376; 510/392; 510/530

[58] Field of Search ..................... 510/302, 305, 510/306, 309, 312, 320, 321, 334, 374, 376, 392, 530

[56] References Cited

U.S. PATENT DOCUMENTS

| | | | |
|---|---|---|---|
| 5,445,755 | 8/1995 | Convents et al. | 252/102 |
| 5,451,337 | 9/1995 | Liu et al. | 252/102 |
| 5,635,104 | 6/1997 | Kott et al. | 252/186.1 |
| 5,700,769 | 12/1997 | Schneider et al. | 510/305 |
| 5,731,280 | 3/1998 | Nielsen et al. | 510/392 |
| 5,801,035 | 9/1998 | Schneider et al. | 435/189 |
| 5,817,495 | 10/1998 | Pedersen et al. | 435/192 |

FOREIGN PATENT DOCUMENTS

| | | |
|---|---|---|
| 1000628 | 11/1976 | Canada . |
| 93/09224 | 5/1993 | WIPO . |
| 94/12621 | 6/1994 | WIPO . |

*Primary Examiner*—Kery Fries
*Attorney, Agent, or Firm*—C. Brant Cook; K. W. Zerby; J. C. Rasser

[57] ABSTRACT

The present invention relates to detergent compositions comprising a cellulase termination composition and cellulase in order to prevent potential tensile strength loss related to the hydrolytic activity of cellulase on cellulose substrates while maintaining the desired benefits from the use of cellulase.

15 Claims, No Drawings

CELLULASE ACTIVITY CONTROL BY A TERMINATOR

FIELD OF THE INVENTION

The present invention relates to detergent compositions comprising a cellulase termination composition and cellulase in order to prevent potential tensile strength loss related to the hydrolytic activity of cellulase on cellulose substrates while maintaining the desired benefits from the use of cellulase.

BACKGROUND OF THE INVENTION

The activity of cellulase is one in which cellulosic fibres or substrates are attacked by the cellulase and depending on the particular function of the cellulase, which can be endo-or exo cellulase and the respective hemicellulases. The cellulose structures are depolymerized or cleaved into smaller and thereby more soluble or dispersible fractures. This activity in particular on fabrics provides a cleaning, rejuvenation, softening and generally improved handfeel characteristics to the structure. This has been previously speculated to be cleavage of fibrils from the surface of fibres such that the main strand of the fibre becomes smoother, less available for incrustations, less likely to entangle with other fibers and optically less defuse in its light reflecting and emission.

Naturally, improvements in the activity of particular cellulase compositions have been made over time in order to allow lower usage or shorter exposure times for similar benefits. In the detergent field cellulases performing in a typical detergent wash environment are available with an activity at which the desired cellulase performance is reached prior to the end of a wash-cycle. However, since the cellulase continues to react, even after having provided the desired performance, cleavage of the cellulose will continue. Therefore, there is a potential risk of tensile strength loss. It should be noted however, tensile strength loss of fabric is also an unavoidable result of mechanical action due to use/wearing and may further result from damage by a bleaching component in the laundry process, especially if the fabric is contaminated with metal compounds.

The obvious solution to the above problem is to use the appropriate amount of cellulase such that the time of a wash-cycle is coinciding with the required time for the desired cellulase performance while tensile strength loss is not yet occuring in a significant amount. This however has proven difficult due to varying wash-cycles depending on local custom, washing machine equipment, cloths and soiling of the cloths be washed, additional additives incorporated into the detergents for other unrelated reasons and degradation of the cellulase upon storage. Therefore a better way to provide the cellulase benefit while preventing fabric damage, is desirable.

According to the present invention, this is provided by including such an amount of cellulase that the desired cellulase activity is certainly achieved prior to the end of the wash-cycle while a cellulase terminator provides the means to prevent potential tensile strength loss within that time.

Cellulase exhibiting exceptionally high activity have been disclosed in the context of compact detergents in WO-92-13057, in the context of quaternary ammonium softening compounds in EP-A-495 554 and in the context of softening clay in a detergent composition in EP-A-495 258 and EP-A-177 165. Cellulase as such with exceptionally high activity has been disclosed in WO 91/17243. Recognition of the potential tensile strength loss of cellulase has been reported in several publications. For example Japanese application J-62-310754 discloses particular cellulases having a specific so-called non-degrading index. Japanese application J-63-134830 discloses detergent compositions for clothing containing a cellulase which has a non-destructive index and U.S. Pat. No. 4,978,470 discloses a detergent composition for closing containing cellulase enzyme with a "non-degrading index" of less than 500.

The attempt to fine tune the cellulase activity to eliminate the problem underlying the present invention as discussed above has its appeal more in the field of industrial cleaning where defined conditions in particular length of fabric exposure to the cellulase, can be assumed. For the typical household conditions, the variation of individual situations encountered, are so multiple that a high activity cellulase together with a terminator is a substantially better approach to ensure the desired cellulase activity thereby preventing potential tensile strength loss of the fabrics.

SUMMARY OF THE INVENTION

The present invention relates to the use of laundry detergent compositions in household fabric treatment machines and handwash treatments. The laundry detergent composition comprises a surface active system, a cellulase enzyme which preferably has a cellulase activity of at least 10CEVU/l of liquid under treatment conditions and a cellulase terminator composition satisfying the criteria of maximum 10% residual activity in a standardized cellulase activity standard test such as the CMC viscosity reduction test and/or the cotton linter test. The cellulase terminator composition is included in the laundry detergent composition at an amount such to control the activity of the cellulase enzyme. The terminator composition used is a bleach terminator comprising a peroxidase with a bleaching system thereby preventing potential tensile strength loss of the fibers. The terminator composition is preferably in the laundry detergent composition in a time-delayed release form.

DETAILED DESCRIPTION OF THE INVENTION

Percentages used hereinafter are by weight unless otherwise stated.

CELLULASE

The activity of enzymes and particularly the activity of cellulase enzyme has been defined for various applications by different analytical methods. These methods all attempt to provide a realistic assessment of the expected in use performance or at least a measurement correlating with the in use performance.

Even so there exist the various different tests for cellulase activity a generally acceptable requirement for cellulase is a minimum viscosity reducing activity on CMC-solutions. Therefore the method of measuring this so-called CMC Endoase activity (in units of 1 CEVU) will be used herein for the preferred cellulases as explained below.

Cellulase preparations particularly useful in the compositions of the invention are those which exhibit a CMC-endoase activity of at least about 10, preferably at least about 20 CEVU/l. In particular, a preferred cellulase exhibits a CMC-endoase activity of at least 25 CEVU/l.

In the present context, the term "CMC-endoase activity" refers to the endoglucanase activity of the endoglucanase component in terms of its ability to degrade cellulose to glucose, cellobiose and triose, as determined by a viscosity decrease of a solution of carboxymethyl cellulose (CMC)

after incubation with the cellulase preparation of the invention, as described in detail below.

The CMC-endoase (endoglucanase) activity can be determined from the viscosity decrease of CMC, as follows a substrate solution is prepared, containing 35 g/l CMC (Hercules 7 LFD) in 0.1 M tris buffer at pH 9.0. The enzyme sample to be analyzed is dissolved in the same buffer. 10ml substrate solution and 0.5 ml enzyme solution are mixed and transferred to a viscosimeter (e.g. Haake VT 181, NV sensor, 181 rpm), thermostated at 40° C. Viscosity readings are taken as soon as possible after mixing and again 30 minutes later. The amount of enzyme that reduced the viscosity to one half under these conditions is defined as 1 unit of CMC-endoase activity, or 1 CEVU/liter.

Another suitable method for testing the activities of the cellulase is the cotton-linter method (see Example II).

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from Humicola insolens. Suitable cellulases are also disclosed in GB-A-2.075.028; GB-A-2.095.275 and DE-OS-2.247.832.

Examples of cellulase components which may be usable in the present invention are:

A cellobiohydrolase component which is immunoreactive with an antibody raised against a highly purified ~70kD cellobiohydrolase (EC 3.2.1.91) derived from Humicola insolens, DSM 1800, or which is a homologue or derivative of the ~70kD cellobiohydrolase exhibiting cellulase activity, or an endoglucanase component which is immunoreactive with an antibody raised against a highly purified ~50kD endoglucanase derived from Humicola insolens, DSM 1800, or which is a homologue or derivative of the ~50kD endoglucanase exhibiting cellulase activity; a preferred endoglucanase component has the amino acid sequence disclosed in PCT Patent Application No. WO91/17244, or an endoglucanase component which is immunoreactive with an antibody raised against a highly purified ~50kD (apparent molecular weight, the amino acid composition corresponds to 45 kD with 2n glycosylation sites) endoglucanase derived from Fusarium oxysporum, DSM 2672, or which is a homologue or derivative of the ~50kD endoglucanase exhibiting cellulase activity; a preferred endoglucanase component has the amino acid sequence disclosed in PCT Patent Application No. WO91/17244, or any of the cellulases disclosed in the published European Patent Application No. EP-A2-271 004, the cellulases having a non-degrading index (NDI) of not less than 500 and being alkalophilic cellulases having an optimum pH not less than 7 or whose relative activity at a pH of not less than 8 is 50% or over of the activity under optimum conditions when carboxy methyl cellulose (CMC) is used as a substrate, or an endoglucanase component which is immunoreactive with an antibody raised against a highly purified ~43kD endoglucanase derived from Humicola insolens, DSM 1800, or which is a homologue or derivative of the ~43kD endoglucanase exhibiting cellulase activity; a preferred endoglucanase component has the amino acid sequence disclosed in PCT Patent Application No. WO 91/17243, or an endoglucanase component which is immunoreactive with an antibody raised against a highly purified ~60kD endoglucanase derived from Bacillus lautus, NCIMB 40250, or which is a homologue or derivative of the ~60kD endoglucanase exhibiting cellulase activity; a preferred endoglucanase component has the amino acid sequence disclosed in PCT Patent Application No. WO 91/10732.

Especially suitable cellulases are the cellulases having color care benefits. Examples of such cellulases are cellulases described in European patent application No. 91202879.2, filed Nov. 6, 1991 (Novo).

According to the present invention, preferred cellulases are those as described in Danish Patent Application 1159/90 or PCT patent application WO91/17243 which is also known as Carezyme(™) available from Novo Nordisk A/S in Bagsvaerd, in Denmark. The cellulase preparation described in these publications and the Carezyme(™) consistent with this description, can consist essentially of a homogeneous endoglucanase component, which is immunoreactive with an anti-body raised against a highly purified 43 kD cellulase derived from Humicola Insulens, DSM 1800, or which is homologous to said 43 kD endoglucanase. An alternative screening for appropriate cellulases for use in the laundry detergent composition according to the present invention is the method specified in EP-A-495 258 or more specifically in EP-A-350 098.

For industrial production of the cellulase preparation herein, however, it is preferred to employ recombinant DNA techniques or other techniques involving adjustments of fermentations or mutation of the microorganisms involved to ensure overproduction of the desired enzymatic activities. Such methods and techniques are known in the art and may readily be carried out by persons skilled in the art.

CELLULASE TERMINATOR COMPOSITION

The cellulase terminator composition comprises a peroxidase, an enhancer and a source of hydrogen peroxide which in combination act to irreversibly terminate the activity of the cellulase after a certain time. The cellulase terminator composition will be referred to as CTC hereinafter.

The function of the CTC is to control the activity of the cellulase in such a way that the activity of the cellulase is more than 90% within 5 minutes from the start of the wash cycle, the cellulase activity is less than 50% within 5 to 10 minutes from the start of the wash cycle and that less than 10% of residual cellulase activity is reached after 15 minutes in the wash cycle. The characteristics of the CTC in absence of the controlled release agent is that it reduces cellulase activity to 10%, preferably 3% of the initial cellulase activity in a standardized cotton linter test within 15 minutes of the wash cycle.

A preferred way to achieve the characteristic of the CTC is to incorporate one or more of the compounds of the CTC in a release agent. Said release agent is an agent which releases the incorporated CTC compound into the wash environment in a controlled manner.

For example, the peroxidase is incorporated in a release agent such that the activity level of said peroxidase within 5 min of the wash cycle is less than 10%. More than 50% activity level of said peroxidase will be reached within the first 5–10 minutes from the start of the wash cycle.

Alternatively, said enhancer and/or said source of hydrogen peroxide may be also incorporated independently into a release agent according to the present invention. In this case, said enhancer and/or said source of hydrogen peroxide may be preferably incorporated independently in a release agent. More preferably, said peroxidase and said enhancer may be incorporated together into a release agent according to the present invention, and said source of hydrogen peroxide may be incorporated independently into another release agent according to the present invention.

Preferably, said peroxidase is in the form of peroxidase-containing granules (in the following sometimes denoted as "peroxidase granulate" or as "peroxidase-containing granulate). Said peroxidase granulate may suitably further contain various granulation aids, binders, fillers, lubricants and the like. Examples hereof include cellulose (e.g. cellulose in fibre or microcrystalline form), dextrins (e.g. yellow dextrin), polyvinylpyrrolidone, polyvinylalcohol, cellulose derivatives (such as CMC or hydroxypropylcellulose), gelatin, salts (e.g. sodium sulfate, sodium chloride, calcium sulfate or calcium carbonate), titanium dioxide, talc and clays (e.g. kaolin or bentonite). Other materials of relevance for incorporation in the granulates of the type in question are described, for example, in EP 0 304 331 B1, and will be well known to persons skilled in the art. Said enhancer and said source of hydrogen peroxide may be also in the form of granulates. As a preferred option, when said enhancer is incorporated into a release agent, said peroxidase and said enhancer are granulated together forming a co-granulate to be incorporated into a release agent. Otherwise, independent enhancer-granulates and (source of hydrogen peroxide)-granulates may be also considered in the cleaning composition according to the present invention.

Methods and apparatus for producing enzyme-containing granulates are likewise well known to the skilled person (see, e.g. EP 0304 331 B1). Compact granulates—produced, e.g., using apparatus comprising knives as described in Example 1 in U.S. Pat. No. 4,106,991—constitute very suitable granulates (co-granulates) in the context of the present invention.

The release agent may be, for example, a coating. Said coating protects said granulates (co-granulates) in the wash environment for a certain period of time. The coating will normally be applied to said granulates (co-granulates) in an amount in the range of 0% to 50% by weight (calculated on the basis of the weight of the uncoated, dry granulate), preferably in the range of 5% to 40% by weight. The amount of coating to be applied to said granulates will depend to a considerable extent on the nature and composition of the desired coating, and to the kind of protection said coating should offer to said granulates. For example, the thickness of said coating or a multi-layered coating applied onto any of the above granulates may determine the period in which the content of said granulates is released. A possible multi-layered coating may be a coating in which, for example, a fast release coating is coated over a slow release coating.

Suitable release coatings are coatings which give rise to release of the contents of the peroxidase- and/or enhancer (co-granulates) and/or (source of hydrogen peroxide)-granulates according to the present invention under the conditions prevailing during the use thereof. Thus, for example, when a preparation of the invention is to be introduced into a washing liquor containing a washing detergent (normally comprising, e.g. one or more types of surfactants), the coating should be one which ensures the release of the contents of said granulates from the release agent when it is introduced into the washing medium.

Preferred release coating are coatings which are substantially insoluble in water. Release coatings which are appropriate in washing media may suitably comprise substances selected from the following: tallow; hydrogenated tallow; partially hydrolyzed tallow; fatty acids and fatty alcohols of natural and synthetic origin; long-chain fatty acid mono-, di- and triesters of glycerol (e.g. glycerol monostearate); ethoxylated fatty alcohols; latexes; hydrocarbons of melting point in the range of 50–80° C.; and waxes. Melt-coating agents are a preferred class of fast or slow release coating agents which can be used without dilution with water. Reference may be made to Controlled Release Systems: Fabrication Technology, Vol. I, CRC Press, 1988, for further information on slow release coating.

Coatings may suitably further comprise substances such as clays (e.g. kaolin), titanium dioxide, pigments, salts (such as calcium carbonate) and the like. The person skilled in the art will be aware of further coating constituents of relevance in the present invention.

In the following, a preparation of a peroxidase-granulate incorporated into a release agent is described.

Granulation 2.0 kg of cellulose fibres (Arbocel™ BC 200), 0.9 kg of kaolin, 1.2 kg of yellow dextrin (TACKIDEX™ G155) and 10.1 kg of sodium sulfate (all dry components) were mixed in a Lödige mixer.

The above mixed dry components were sprayed, with continuous mixing, with 2.1 kg of liquid peroxidase concentrate (71 mg enzyme protein/g; Coprinus peroxidase produced as described in Example 1 in EP 505 311) to which had been added (and dissolved) 0.5 kg of sucrose and 0.8 kg of water.

During and after spraying, a compact peroxidase-granulate was formed by means of the knives described in Example 1 in U.S. Pat. No. 4,106,991.

When the granulation was finished, the peroxidase-granulate was dried on a fluidized bed. The dry peroxidase-granulate was sieved, and the product fraction of size between 300 and 1000 mm was separated for coating.

Coating

A peroxidase-granulate incorporated into a fast release agent is, for example, an uncoated peroxidase-granulate. A peroxidase-granulate incorporated into a slow release agent may be made in the following manner. The peroxidase-granulate to be incorporated into a slow release agent was heated to 60° C. in a Lödige mixer, and 5% of glycerol monostearate (also heated to 60° C.) was added under continuous mixing. When the glycerol monostearate was distributed, the peroxidase-granulate was powdered with 6.7% of organoclay (Claytone™ AF) and 6.7% of titanium dioxide under continuous mixing. All percentages are weight percentages relative to the dry uncoated peroxidase-granulate. After cooling, the coated peroxidase-granulate, i.e. the peroxidase-granulate incorporated into slow release agent, was sieved and the fraction in the size range 300–1100 mm was collected for use.

The CTC is used in the laundry detergent composition in an appropriate amount, preferably below 10% by weight. Naturally the "appropriate amount" strongly depends on the effectiveness of the CTC, the activity of the cellulase, the surfactant system and its interaction with the cellulase. Therefore the amount of CTC is a function of the other compounds of the detergent composition and the washing conditions. The amount in accordance with the present invention is selected such that for example in European washing conditions the cellulase activity of the selected cellulase is reduced to 10% of the initial cellulase within 15 minutes from the start of the wash cycle.

CTC COMPOSITION

The CTC composition according to the present invention comprises a peroxidase, an enhancer and a source of hydrogen peroxidase.

Peroxidase enzymes (EC 1.11.1) employed in the context of the invention may very suitably be, e.g., any peroxidase comprised by the enzyme classification EC 1.11.1.7; peroxidase fragments, exhibiting peroxidase activity, as well as synthetic or semi-synthetic peroxidase derivatives [e.g. with porphyrin ring systems], or microperoxidases (see, e.g., U.S. Pat. No. 4,077,768, EP 0 537 381, WO 91/05858 and WO 92/16634)] are also relevant in the context of the invention. Suitable peroxidases are known from microbial, plant and animal origins. Other possible peroxidase enzymes may be derived with protein engineering methods where one or several amino acids of the natural peroxidase enzyme may have been replaced by other amino acids.

Preferably, the peroxidase employed in the method of the present invention may be produced by plants (e.g. horseradish or soy bean peroxidase) or micro-organisms such as fungi or bacteria. Some preferred fungi include strains belonging to the subdivision Deuteromycotina, class Hyphomycetes, e.g. Fusarium, Humicola, Tricoderma, Myrothecium, Verticillum, Arthromyces, Caldariomyces, Ulocladium, Embellisia, Cladosprorium or Dreschlera, in particular *Fusarium oxysporum* (DSM 2672), *Humicola insolens, Trichoderma resii, Myrothecium verrucana* (IFO 6113), *Verticillum alalboatrum, Verticillum dahlie, Arthromyces ramosus* (FERM P-7754), *Caldariomyces fumago, Ulocladium chartarum, Embellisia alli* or *Dreschlera halodes.*

Other preferred fungi include strains belonging to the subdivision Basidiomycotina, class Basidiomycetes, e.g. Coprinus, Phanerochaete, Coriolus or Trametes, in particular *Coprinus cinereus* f. microsporus (IFO 8371), *Coprinus macrorhizus, Phanerochaete chrysosporium* (e.g. NA-12) or Trametes (previously called Polyporus), e.g. T. versicolor (e.g. PR428-A). Further preferred fungi include strains belonging to the subdivision Zygomycotina, class Mycoraceae, e.g. Rhizopus or Mucor, in particular *Mucor hiemalis.*

Some preferred bacteria include strains of the order Actinomycetales, e.g. *Streptomyces spheroides* (ATTC 23965), *Streptomyces thermoviolaceus* (IFO 12382) or *Streptoverticillum verticillium ssp.* verticillium. Other preferred bacteria include *Bacillus pumilus* (ATCC 12905), *Bacillus stearothermophilus,* Rhodobactersphaeroides, *Rhodomonas palustri, Streptococcus lactis, Pseudomonas purrocinia* (ATCC 15958) or *Pseudomonas fluorescens* (NRRL B-11). Further preferred bacteria include strains belonging to Myxococcus, e.g. M. virescens.

Other relevant peroxidases are "haloperoxidases" (see, e.g., U.S. Pat. No. 4,937,192), such as chloride peroxidases (EC 1.11.1.10), bromide peroxidases, and iodide peroxidases (EC 1.11.1.8). Other potential sources of useful peroxidases are listed in B. C. Saunders et al., Peroxidase, London, 1964, pp. 41–43.

The peroxidase may furthermore be one which may be produced by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture. Particularly, a peroxidase produced in a recombinant manner is a peroxidase derived from a Coprinus po., in particular *C. macrorhizus* or *C. cinereus* according to WO 92/16634.

As already indicated to some extent above, the term peroxidase as employed in the context of the invention embraces substances possessing peroxidase activity, such as peroxidase-active fragments derived from cytochromes, hemoglobin or peroxidase enzymes, and synthetic or semi-synthetic derivatives thereof, e.g. iron porphins, iron porphyrins and iron phthalocyanine and derivatives thereof. The peroxidase employed in a preparation of the invention will very suitable often be a Coprinus peroxidase, a Myxococcus peroxidase, or a horseradish peroxidase.

Enhancers

The enhancer can be any suitable peroxidase enhancer. Examples of enhancers include the following: halide ions (e.g. chloride and bromide); certain metal ions (e.g. $Mn^{2+}$); phenolic species (e.g. p-hydroxycinnamic acid 2,4-dichlorophenol, vanillin, 7-hydroxycoumarin, 6-hydroxy-2-naphtoic acid, and p-hydroxybenzenesulfonate); 2,2-azino-bis (3-ethylbenzothiazoline-6-sulfonate (ABTS; see, e.g., WO 94/12620); and 10-methyl-, 10-ethyl- and 10-propyl-phenothiazine (see, e.g., WO 94/12621). Numerous other enhancers or enhancing agents are disclosed in WO 94/12619, WO 94/12620 and WO 94/12621.

Preferred enhancers in the context of the present invention are 10-phenothiazinepropionic acid (PPT), 10-ethylphenothiazine-4-carboxylic acid (EPC), 10-phenoxazinepropionic acid (POP) and 10-methylphenoxazine (described in WO 94/12621), and dye-transfer inhibitory co-granulate preparations of the invention comprising such enhancers have good storage stability (shelf life), and lead to very satisfactory dye-transfer inhibition in fabric washing (vide infra).

Source of hydrogen peroxide

The bleaches suitable for the present invention include sources of peroxygen bleaches. Examples of suitable sources of peroxygen bleaches include hydrogen peroxide releasing agents such as hydrogen peroxide, perborates, e.g. perborate monohydrate, perborate tetrahydrate, persulfates, percarbonates, peroxydisulfates, perphosphates and peroxyhydrates. Preferred bleaches are percarbonates and perborates.

The hydrogen peroxide releasing agents can be used in combination with bleach activators such as tetraacetylethylenediamine (TAED), nonanoyloxybenzene-sulfonate (NOBS, described in U.S. Pat. No. 4,412,934), 3,5,5-trimethylhexanoloxybenzenesulfonate (ISONOES, described in EP 120,591), or pentaacetylglucose (PAG), which are perhydrolyzed to form a peracid as the active bleaching species, leading to improved bleaching effect.

It may be also desirable to utilize an enzymatic process for hydrogen peroxide formation. Thus, the process according to the invention may additionally comprise adding an enzymatic system (i.e. an enzyme and a substrate therefore) which is capable of generating hydrogen peroxide during the washing process.

One such category of hydrogen peroxide generating systems comprises enzymes which are able to convert molecular oxygen and an organic or inorganic substrate into hydrogen peroxide and the oxidized substrate respectively. These enzymes produce only low levels of hydrogen peroxide, but they may be employed to great advantage in the process of the invention as the presence of peroxidase ensures an efficient utilization of the hydrogen peroxide produced.

Preferred hydrogen peroxide-generating enzymes are those which act on cheap and readily available substrates which may conveniently be included into detergent compositions. An example of such a substrate is glucose which may be utilized for hydrogen peroxide production by means of glucose oxidase. Suitable oxidases include those which act on aromatic compounds such as phenols and related substances. Other suitable oxidases are urate oxidase, galactose oxidase, alcohol oxidases, amine oxidases, amino acid oxidase, amyloglucosidase, and cholesterol oxidase.

The preferred enzymatic systems are alcohol and aldehyde oxidases. The more preferred systems for granular detergent application would have solid alcohols, e.g. glucose whose oxidation is catalysed by glucose oxidase to glucoronic acid with the formation of hydrogen peroxide. The more preferred systems for liquid detergent application would involve liquid alcohols which could also act as, for example, solvents. An example is ethanol/ethanol oxidase. Such enzymatic systems are disclosed in EP Patent Application 91202655.6 filed Oct. 9, 1991.

Other peroxygen bleaches suitable for the present invention include organic peroxyacids such as percarboxylic acids.

Detergent Components

The detergent compositions of the invention may also contain additional detergent components. The precise nature of these additional components, and levels of incorporation thereof will depend on the physical form of the composition, and the nature of the cleaning operation for which it is to be used.

The compositions of the invention may for example, be formulated as hand and machine laundry detergent compositions including laundry additive compositions and compositions suitable for use in the pretreatment of stained fabrics, rinse added fabric softener compositions, and compositions for use in general household hard surface cleaning operations.

When formulated as compositions suitable for use in a machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components.

If needed the density of the laundry detergent compositions herein ranges from 550 to 1000 g/liter, preferably 600 to 950 g/liter of composition measured at 20° C. The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition.

In the compact compositions, the filler salt is present in amounts not exceeding 15% of the total composition, preferably not exceeding 10%, most preferably not exceeding 5% by weight of the composition.

The inorganic filler salts, such as meant in the present compositions are selected from the alkali and alkaline-earth-metal salts of sulphates and chlorides.

A preferred filler salt is sodium sulphate.

Surfactant System

The detergent compositions according to the present invention comprise a surfactant system wherein the surfactant can be selected from nonionic and/or anionic and/or cationic and/or ampholytic and/or zwitterionic and/or semipolar surfactants.

The surfactant is typically present at a level of from 0.1% to 60% by weight. More preferred levels of incorporation are 1% to 35% by weight, most preferably from 1% to 20% by weight of machine dishwashing, laundry and rinse added fabric softener compositions in accord with the invention, and from 5% to 60% by weight, more preferably from 15% to 45% by weight of manual dishwashing compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Preferred non-alkylbenzene sulfonate surfactant systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA O5O (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units. The preferred alkylpolyglycosides have the formula

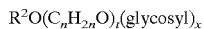

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula.

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

When included in such laundry detergent compositions, the nonionic surfactant systems of the present invention act to improve the greasy/oily stain removal properties of such laundry detergent compositions across a broad range of laundry conditions.

Highly preferred anionic surfactants include alkyl alkoxylated sulfate surfactants hereof are water soluble salts or acids of the formula RO(A)$_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethylammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$E(2.25)M), $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $O_{03}$ according to "The Journal of the American Oil Chemists Society", 52 (1975), pp. 323–329. Suitable starting materials would include natural fatty substances as derived from tallow, palm oil, etc. The preferred alkyl ester sulfonate surfactant, especially for laundry applications, comprise alkyl ester sulfonate surfactants of the structural formula:

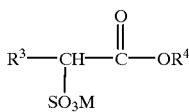

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference). When included therein, the laundry detergent compositions of the present invention typically comprise from about 1% to about 40%, preferably from about 3% to about 20% by weight of such anionic surfactants.

It has been found that the CTC is very efficient at anionic/nonionic ratio between 10:1 to 1:2.

The laundry detergent compositions of the present invention may also contain cationic, ampholytic, zwitterionic, and semi-polar surfactants, as well as the nonionic and/or anionic surfactants other than those already described herein. Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

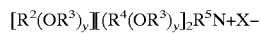

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Highly preferred cationic surfactants are the water-soluble quaternary ammonium compounds useful in the present composition having the formula:

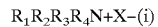

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl. The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions. Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;
lauryl dimethyl (ethenoxy)$_4$ ammonium chloride or bromide;
choline esters (compounds of formula (i) wherein R$_1$ is CH$_2$–CH$_2$—O—C—C$_{12-14}$ alkyl and R$_2$R$_3$R$_4$ are methyl).

CH$_2$—CH$_2$—O—C—C$_{12-14}$ alkyl and R$_2$R$_3$R$_4$ are methyl).
∥
O di-alkyl imidazolines [compounds of formula (i)].

Other cationic surfactants useful herein are also described in U.S. Pat. No. 4,228,044, Cambre, issued Oct. 14, 1980 and in European Patent Application EP 000,224.

When included therein, the laundry detergent compositions of the present invention typically comprise from 0.2% to about 25%, preferably from about 1% to about 8% by weight of such cationic surfactants. It has been found that the combination of cationic surfactants, cellulase and CTC leads to synergistic improvements in softening and cleaning.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms. Semi-polar nonionic detergent surfactants include the amine oxide surfactants having the formula

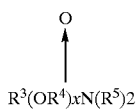

R$^3$(OR$^4$)$x$N(R$^5$)$_2$ wherein R$^3$ is an alkyl, hydroxyalkyl, or alkyl phenyl group or mixtures thereof containing from about 8 to about 22 carbon atoms; R$^4$ is an alkylene or hydroxyalkylene group containing from about 2 to about 3 carbon atoms or mixtures thereof; x is from 0 to about 3; and each R$^5$ is an alkyl or hydroxyalkyl group containing from about 1 to about 3 carbon atoms or a polyethylene oxide group containing from about 1 to about 3 ethylene oxide groups. The R$^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Optional Deterrent Ingredients:

Preferred detergent compositions of the present invention may further comprise an enzyme which provides cleaning performance and/or fabric care benefits. Said enzymes include enzymes selected from proteases, gluco-amylases, amylases, lipases, cutinases, pectinases, reductases, oxidases, phenoloxidases, lipoxygenases, ligninases, pullulanases, tannases, pentosanases, malanases, β-glucanases, arabinosidases or mixtures thereof.

A preferred combination is a cleaning composition having cocktail of conventional applicable enzymes like protease, amylase, lipase, cutinase in conjunction with one or more plant cell wall degrading enzymes.

Preferred commercially available protease enzymes include those sold under the tradenames Alcalase, Savinase, Primase, Durazym, and Esperase by Novo Nordisk A/S (Denmark), those sold under the tradename Maxatase, Maxacal and Maxapem by Gist-Brocades, those sold by Genencor International, and those sold under the tradename Opticlean and Optimase by Solvay Enzymes. Also proteases described in our co-pending application U.S. Ser. No. 08/136,797 can be included in the detergent composition of the invention. Protease enzyme may be incorporated into the compositions in accordance with the invention at a level of from 0.000% to 2% active enzyme by weight of the composition. It has been found that the combination of proteases, cellulase and CTC leads to improved wool and silk rejuvenation caused by the CTC effect on the protease.

Other preferred enzymes that can be included in the detergent compositions of the present invention include lipases. Suitable lipase enzymes for detergent usage include those produced by microorganisms of the Pseudomonas group, such as Pseudomonas stutzeri ATCC 19.154, as disclosed in British Patent 1,372,034. Suitable lipases include those which show a positive immunological cross-reaction with the antibody of the lipase, produced by the microorganism *Pseudomonas fluorescent* IAM 1057. This lipase is available from Amano Pharmaceutical Co. Ltd., Nagoya, Japan, under the trade name Lipase P "Amano," hereinafter referred to as "Amano-P". Especially suitable lipases are lipases such as M1 Lipase$^R$ and Lipomax$^R$ (Gist-Brocades) and Lipolase$^R$ (Novo) which have found to be very effective when used in combination with the compositions of the present invention. Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor). The lipases and/or cutinases are normally incorporated in the detergent composition at levels from 0.0001% to 2% of active enzyme by weight of the detergent composition.

Amylases (& and/or β) can be included for removal of carbohydrate-based stains. Suitable amylases are Termamy$^1$R (Novo Nordisk), Fungamyl$^R$ and BAN$^R$ (Novo Nordisk). The above-mentioned enzymes may be of any suitable origin, such as vegetable, animal, bacterial, fungal and yeast origin. Said enzymes are normally incorporated in the detergent composition at levels from 0.0001% to 2% of active enzyme by weight of the detergent composition. Other suitable detergent ingredients that can be added are enzyme oxidation scavengers which are described in Copending European Patent application 92870018.6 filed on Jan. 31, 1992. Examples of such enzyme oxidation scavengers are ethoxylated tetraethylene polyamines.

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetracarboxylates, cyclopentadienide pentacarboxylates, 2,3,4,5-tetrahydro-furan-cis, cis, cis-tetracarboxylates, 2,5-tetrahydro-furan-cis -dicarboxylates, 2,2,5,5-tetrahydrofuran-tetracarboxylates, 1,2,3,4,5,6-hexane-hexacar-boxylates and and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343.

Of the above, the preferred polycarboxylates are hydroxy-carboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention. Said chelants, in combination with cellulase and CTC, have found to synergistically improve the cleaning performance.

Preferred builder systems include a mixture of a water-insoluble aluminosilicate builder such as zeolite A, and a watersoluble carboxylate chelating agent such as citric acid. Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms. Combination of cellulase, CTC and the above polymers leads to significally reduced inorganic encrustation. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 10% to 80% by weight of the composition preferably from 20% to 70% and most usually from 30% to 60% by weight.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2 646 126 published Apr. 28, 1977. An example of such a compound is DC-544, commercially available from Dow Corning, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R. Such suds suppressor system are described in Copending European Patent application N 92870174.7 filed 10 November, 1992.

Especially preferred silicone suds controlling agents are described in Copending European Patent application NO92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight. Other components used in detergent compositions may be employed, such as soil-suspending agents, soil-release agents, optical brighteners, abrasives, bactericides, tarnish inhibitors, coloring agents, and/or encapsulated or non-encapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid-esters of substituted dicarboxylic acids such as described in U.S. Pat. No. 3,455,838. These acid-ester dextrins are,preferably, prepared from such starches as waxy maize, waxy sorghum, sago, tapioca and potato. Suitable examples of said encapsulating materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4, -4'-bis-( 2-morpholino-4-anilino-s-triazin-6-ylamino-stilbene-2:2'-disulphonate, disodium 4,4'-bis-(2,4-dianilino-s-triazin-6-ylamino)stilbene-2:2'disulphonate, monosodium 4',4"-bis-(2,4-dianilino-s-triazin-6ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2,1,3-triazol-2-yl)-stilbene-2,2'disuiphonate, di-so-dium 4,4'bis(2-anilino-4-(1-methyl-2-hydroxyethylamino)-s-triazin-6-ylami-no)stilbene-2,2'disulphonate, sodium 2(stilbyl-4"-(naphtho-1',2':4,5)-1,2,3-triazole-2"-sulphonate and 4,4'-bis(2-sulphostyryl)biphenyl. Highly preferred brighteners are the specific brighteners of copending European Patent application No. 95201943.8.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4,116,885 and 4,711,730 and European Published Patent Application No. 0 272 033. A particular preferred polymer in accordance with EP-A-0 272 033 has the formula:

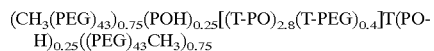

where PEG is —(OC$_2$H$_4$)O—,PO is (OC$_3$H$_6$O) and T is (pcOC$_6$H$_4$ CO).

Also very useful are modified polyesters as random copolymers of dimethyl terephthalate, dimethyl sulfoisophthalate, ethylene glycol and 1–2 propane diol, the end groups consisting primarily of sulphobenzoate and secondarily of mono esters of ethylene glycol and/or propane-diol. The target is to obtain a polymer capped at both end by sulphobenzoate groups, "primarily", in the present context most of said copolymers herein will be end-capped by sulphobenzoate groups. However, some copolymers will be less than fully capped, and therefore their end groups may consist of monoester of ethylene glycol and/or propane 1–2 diol, thereof consist "secondarily" of such species.

The selected polyesters herein contain about 46% by weight of dimethyl terephthalic acid, about 16% by weight of propane −1.2 diol, about 10 by weight ethylene glycol about 13% by weight of dimethyl sulfobenzoic acid and about 15% by weight of sulfoisophthalic acid, and have a molecular weight of about 3.000. The polyesters and their method of preparation are described in detail in EPA 311 342. The combination of cellulase, CTC and polyesters have found to synergistically improve the whiteness and color maintenance.

Softening Agents

Fabric softening agents can also be incorporated into laundry detergent compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B011 340 and their combination with mono C$_{12}$–C$_{14}$ quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition. It has been found that the softeness performance of the combination of cellulase and smectite clay and CTC is synergistically enhanced.

Dye Transfer Inhibition

The present invention also relates to a process for inhibiting dye transfer from one fabric to another of solubilized and suspended dyes encountered during fabric laundering operations involving colored fabrics. It has been found that the combination of cellulase, polymeric dye transfer inhibiting agents and CTC leads to synergistic improvement in color whiteness and maintenance.

Polymeric Dye Transfer Inhibiting Agents

The detergent compositions according to the present invention also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash. Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof. Addition of such polymers also enhances the performance of the enzymes.

a) Polyamine N-oxide Polymers

The polyamine N-oxide polymers suitable for use contain units having the following structure formula:

$$\begin{array}{c} P \\ | \\ A_x \\ | \\ R \end{array} \quad (I)$$

wherein P is a polymerisable unit, whereto the R—N—O group can be attached to or wherein the R—N—O group forms part of the polymerisable unit or a combination of both.

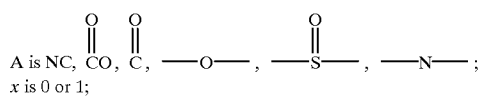

A is NC, CO, C, —O—, —S—, —N—;
x is 0 or 1;

R are aliphatic, ethoxylated aliphatics, aromatic, heterocyclic or alicyclic groups or any combination thereof whereto the nitrogen of the N-O group can be attached or wherein the nitrogen of the N-O group is part of these groups.

The N-O group can be represented by the following general structures:

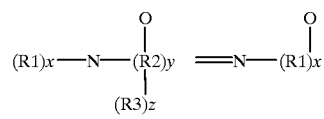

wherein R1, R2, and R3 are aliphatic groups, aromatic, heterocyclic or alicyclic groups or combinations thereof, x or/and y or/and z is 0 or 1 and wherein the nitrogen of the N-O group can be attached or wherein the nitrogen of the N-O group forms part of these groups.

The N-O group can be part of the polymerisable unit (P) or can be attached to the polymeric backbone or a combination of both. Suitable polyamine N-oxides wherein the N-O group forms part of the polymerisable unit comprise polyamine N-oxides wherein R is selected from aliphatic, aromatic, alicyclic or heterocyclic groups. One class of said polyamine N-oxides comprises the group of polyamine N-oxides wherein the nitrogen of the N-O group forms part of the R-group. Preferred polyamine N-oxides are those wherein R is a heterocyclic group such as pyrridine, pyrrole, imidazole, pyrrolidine, piperidine, quinoline, acridine and derivatives thereof. Another class of said polyamine N-oxides comprises the group of polyamine N-oxides wherein the nitrogen of the N-O group is attached to the R-group.

Other suitable polyamine N-oxides are the polyamine oxides whereto the N—O group is attached to the polymerisable unit. Preferred class of these polyamine N-oxides are the polyamine N-oxides having the general formula (I) wherein R is an aromatic, heterocyclic or alicyclic groups wherein the nitrogen of the N—O functional group is part of said R group. Examples of these classes are polyamine oxides wherein R is a heterocyclic compound such as pyrridine, pyrrole, imidazole and derivatives thereof. Another preferred class of polyamine N-oxides are the polyamine oxides having the general formula (I) wherein R are aromatic, heterocyclic or alicyclic groups wherein the nitrogen of the N—O functional group is attached to said R groups.

Examples of these classes are polyamine oxides wherein R groups can be aromatic such as phenyl.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers of the present invention typically have a ratio of amine to the amine N-oxide of 10:1 to 1:1000000. However the amount of amine oxide groups present in the polyamine oxide polymer can be varied by appropriate copolymerization or by appropriate degree of N-oxidation. Preferably, the ratio of amine to amine N-oxide is from 2:3 to 1:1000000. More preferably from 1:4 to 1:1000000, most preferably from 1:7 to 1:1000000. The polymers of the present invention actually encompass random or block copolymers where one monomer type is an amine N-oxide and the other monomer type is either an amine N-oxide or not. The amine oxide unit of the polyamine N-oxides has a PKa<10, preferably PKa<7, more preferred PKa<6. The polyamine oxides can be obtained in almost any degree of polymerisation. The degree of polymerisation is not critical provided the material has the desired water-solubility and dye-suspending power.

Typically, the average molecular weight is within the range of 500 to 1000,000; preferably from 1,000 to 50,000, more preferably from 2,000 to 30,000, most preferably from 3,000 to 20,000.

b) Copolymers of N-vinylpyrrolidone and N-vinylimidazole

The N-vinylimidazole N-vinylpyrrolidone polymers used in the present invention have an average molecular weight range from 5,000–1,000,000, preferably from 20,000–200,000.

Highly preferred polymers for use in detergent compositions according to the present invention comprise a polymer selected from N-vinylimidazole N-vinylpyrrolidone copolymers wherein said polymer has an average molecular weight range from 5,000 to 50,000 more preferably from 8,000 to 30,000, most preferably from 10,000 to 20,000. The average molecular weight range was determined by light scattering as described in Barth H. G. and Mays J. W. Chemical Analysis Vol 113, "Modern Methods of Polymer Characterization". Highly preferred N-vinylimidazole N-vinylpyrrolidone copolymers have an average molecular weight range from 5,000 to 50,000; more preferably from 8,000 to 30,000; most preferably from 10,000 to 20,000.

The N-vinylimidazole N-vinylpyrrolidone copolymers characterized by having said average molecular weight range provide excellent dye transfer inhibiting properties while not adversely affecting the cleaning performance of detergent compositions formulated therewith. The N-vinylimidazole N-vinylpyrrolidone copolymer of the present invention has a molar ratio of N-vinylimidazole to N-vinylpyrrolidone from 1 to 0.2, more preferably from 0.8 to 0.3, most preferably from 0.6 to 0.4.

c) Polyvinylpyrrolidone

The detergent compositions of the present invention may also utilize polyvinylpyrrolidone ("PVP") having an average molecular weight of from about 2,500 to about 400,000, preferably from about 5,000 to about 200,000, more preferably from about 5,000 to about 50,000, and most preferably from about 5,000 to about 15,000. Suitable polyvinylpyrrolidones are commercially vailable from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). Other suitable polyvinylpyrrolidones which are commercially available from BASF Cooperation include Sokalan HP 165 and Sokalan HP 12; polyvinylpyrrolidones known to persons skilled in the detergent field (see for example EP-A-262,897 and EP-A-256,696).

d) Polyvinyloxazolidones:

The detergent compositions of the present invention may also utilize polyvinyloxazolidone as a polymeric dye transfer inhibiting agent. Said polyvinyloxazolidones have an average molecular weight of from about 2,500 to about 400,000, preferably from about 5,000 to about 200,000, more preferably from about 5,000 to about 50,000, and most preferably from about 5,000 to about 15,000.

e) Polyvinylimidazole:

The detergent compositions of the present invention may also utilize polyvinylimidazole as polymeric dye transfer inhibiting agent. Said polyvinylimidazoles have an average about 2,500 to about 400,000, preferably from about 5,000 to about 200,000, more preferably from about 5,000 to about 50,000, and most preferably from about 5,000 to about 15,000.

Method of washing

The process described herein comprises contacting fabrics with a laundering solution in the usual manner and exemplified hereunder.

The process of the invention is conveniently carried out in the course of the cleaning process. The method of cleaning is preferably carried out at 5° C. to 95° C., especially between 10° C. and 60° C. The pH of the treatment solution is preferably from 7 to 11, especially from 7.5 to 10.5. Highly preferred pH is between 9 to 10.5.

The following examples are meant to exemplify compositions of the present invention, but are not necessarily meant to limit or otherwise define the scope of the invention.

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SAS: $C_{12}$–$C_{14}$ secondary (2,3) alkyl sulfate in the form of the sodium salt.

APG: Alkyl polyglycoside surfactant of formula $C_{12}$-(glycosyl)$_x$, where x is 1.5, AEC: Alkyl ethoxycarboxylate surfactant of formula $C_{12}$ ethoxy (2) carboxylate.

SS Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS $C_{1X}$–$C_{1Y}$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}$–$C_{14}$ alkyl N-methyl glucamide TFAA: $C_{16}$–$C_{18}$ alkyl N-methyl glucamide.

Silicate: Amorphous Sodium Silicate ($SiO_2$:$Na_2O$ ratio=2.0)

NaSKS-6: Crystalline layered silicate of formula $\delta$-$Na_2Si_2O_5$

Carbonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF GmbH Zeolite A: Hydrated Sodium Aluminosilicate of formula $Na_{12}(AlO_2SiO_2)_{12}$. $27H_2O$ having a primary particle size in the range from 1 to 10 micrometers Zeolite MAP: Alkali metal alumino-silicate of the zeolite P type having a silicon to aluminium ratio not greater than 1.33

Citrate: Tri-sodium citrate dihydrate

Citric: Citric Acid

Perborate: Anhydrous sodium perborate monohydrate bleach, empirical formula $NaBO_2$. $H_2O_2$ PB4: Anhydrous sodium perborate tetrahydrate Percarbonate: Anhydrous sodium percarbonate bleach of empirical formula $2Na_2CO_3$. $3H_2O_2$ TAED: Tetraacetyl ethylene diamine Paraffin: Paraffin oil sold under the tradename Winog 70 by Wintershall.

Amylase: Amylolytic enzyme sold under the tradename Termamyl by Novo Nordisk A/S Lipase: Lipolytic enzyme sold under the tradename Lipolase, Lipolase Ultra by Novo Nordisk A/S Peroxidase: Peroxidase enzyme POD Cellulase: Cellulosic enzyme sold under the tradename Carezyme or Celluzyme by Novo Nordisk A/S. Carezyme 1T (1000 CEVU/g) Celluzyme 1T (1000 CEVU/g)

CMC: Sodium carboxymethyl cellulose

HEDP: 1,1-hydroxyethane diphosphonic acid

DETPMP: Diethylene triamine penta (methylene phosphonic acid), marketed by Monsanto under the Trade name Dequest PVP: Polyvinyl pyrrolidone polymer
EDDS: Ethylenediamine -N, N'-disuccinic acid, [S,S] isomer in the form of the sodium salt.
Suds Suppressor: 25% paraffin wax Mpt 50° C., 17% hydrophobic silica, 58% paraffin oil.
Granular Suds Suppressor: 12% Silicone/silica, 18% stearyl alcohol, 70% starch in granular form
SCS: Sodium cumene sulphonate
CTC: Coprinus cinereus peroxidase 0.3 POXU/ml PPT 4 M PB1 0.5% with release agent (Glycerolstearate coating)
CTCI: 0.5% PB1 POD (2 PODU/ml) 50 M phenolsulfonate
Sulphate: Anhydrous sodium sulphate.
HMWPEO: High molecular weight polyethylene oxide
PGMS: Polyglycerol monostearate having a tradename of Radiasurf 248
TAE 25: Tallow alcohol ethoxylate (25)
PEG-6: Polyethylene glycol having a molecular weight of 600.

EXAMPLE 1

A granular detergent was prepared according to a composition without CTCI in example 6d. The POD granulates in CTCI were applied without release agent. The following wash tests were carried out:
Conditions:
Miele washing machine W756
40° C. wash cycle
water hardness: 15 grains/US gallon
detergent usage: 120 g per wash
  pH=8.5 (in wash liquor)
load composition: 2 kg cotton/polycotton fabrics tracers to assess color rejuvenation; tracers were pilled cotton fabrics
WFK 11A test fabrics to measure tensile strength loss.
Cellulase concentration: 165 CEVU/l Carezyme IT Fabrics were washed for 12 wash cycles and then assessed for color rejuvenation and tensile strength. The CTCI system was added to the wash after 0 min (treatment B), 5 min (treatment C), 10 min (treatment D).

| Treatment | Color rejuvenation* | Tensile strength loss** |
|---|---|---|
| A no CTCI | 3.5 psu | 130 |
| B CTCI added after 0 min | 1.9 psu | 95 |
| C CTCI added after 5 min | 3.0 psu | 105 |
| D CTCI added after 10 min | 3.7 psu | 111 |
| E (treatment w/o cellulase and CTCI) | reference | 100 |

*0–4 panel score unit (Scheffe scale)
0 = no difference, 4 = big improvement compared to treatment E difference of 0.8 is statistically significant at 95% confidence level
**Normalised tensile strength loss: difference of 10% is statistically significant at 95% confidence level.

The test proves that treatments A, C, D deliver the same high colour rejuvenation benefits whereas treatment B is deficient.

Treatment A, however, leads to significantly higher tensile strength loss than treatments C and D. The optimum release profile for the CTCI system therefore is between 5–10 minutes delivering equal benefit to A and no meaningful increase in tensile strength loss versus a nil-cellulase treatment E.

EXAMPLE 2

The following washing machine test was performed. The first treatment corresponds to a reference treatment where a level of cellulase of 10 CEVU/L is tested in absence CTC. The treatment 2 has the same level of cellulase and a CTC (described in 3). Treatment 3 is the same as treatment 2 except that the CTC is not controlled released. Cellulase activity is monitored during the test via a method described in (2).

| Minutes in the wash[4]: | | | Cellulase [1]Activity[2] in the wash | | |
|---|---|---|---|---|---|
| Treatment: | CTC[3] | Control Release | 0–5 | 5–10 | >10 |
| 1 | No | — | 100 | 85 | 80 |
| 2 | Yes | Yes | 100 | 5 | 0 |
| 3 | Yes | No | 5 | 0 | 0 |

[1]The cellulase is Carezyme ™ supplied by Novo Nordisk. Activity of the enzyme granulate is 1000 Cevu/g.
[2]The cellulase activity is quantified in a detergent matrix (5) by a two-step procedure. The β-1-4 glycoside bonds of insoluble cellulose (cotton linters) are hydrolysed randomly by the cellulase in the presence of cellobiase, to yield D-Glucose. The concentration of D-glucose, which is proportional to the cellulase activity is measured indirectly by spectrophotometry at 340 nm using an Abbott commercial enzymatic testkit (hexokinase and glucose-6-phosphatedehydrogenase in the presence of NAD+. Standard Carezyme ™ is used for calibration and the results are expressed as % of standard Carezyme ™.
[3]Description of the: CTC system: Peroxidase derived from *Coprinus cinereous* is suppiied by Novo Nordisk. The concentration of peroxidase enzyme in the wash is 0.3 POXU/ml. The peroxidase enzyme is delivered in the form of a control release granulate (activity of the granulate is 30 KPOXU/g). The enhancer is PPT (phenothiazine-10-propionic acid). The concentration of PPT accelerator is 4 $\mu$M, concentration of PB1 in the wash is 35 ppm.Source of hydrogen peroxide is perborate mono-hydrate (PB1).
[4]Test conditions: The granular detergent is added via an granulette to a Miele washing machine. Detergent (6) concentration in the wash liquor is 8000 ppm. Wash conditions are as follows: water temperature is 40° C., water hardness is 8 grain/US gallon. Tests are run in absence of load.
[5]The composition of the detergent used in the test is described in the table below. Non-ionic surfactant system used is a 2.7:1 mixture of Marlipal 24/50 (C24EO5) and C16/C18 glucose amide. HLB of these surfactant has been measured to be $\geq$10. The pH of the detergent has been measured in the wash to be 9.5.

| | % by weight of the total formula |
|---|---|
| 45AS | 8.5 |
| 25E3S | 2.1 |
| 24E5 | 7.1 |
| C16/C18 glucose amide | 2.6 |
| Zeolite | 23.1 |
| Citrate | 7.7 |
| citric acid | 5.3 |
| Na-SKS-6 | 7.5 |
| Carbonate | 3.1 |
| Bicarbonate | 4.0 |
| Sulfate | 5.94 |
| Polyacrylate | 5.1 |
| CMC | 0.36 |
| PVNO/PVPVI | 0.19 |
| Protease | 0.87 |
| Lipase | 0.24 |
| Amylase | 0.8 |
| EDDS | 0.5 |
| Suds suppresser | 0.41 |
| Water and miscellaneous | Balance |

The test results show that reference treatment 1 has relatively stable cellulase activity in the wash. Treatment 2 which incorporates the controlled release CTC, shows full cellulase activity for the first 5 minutes of the wash. After 5 minutes, the CTC is released and deactivates the cellulase. Treatment 3 however, shows a significant loss of cellulase activity right from the start of the wash. As a result, treatment 3 is deficient. Therefore, treatment 2 which contains the controlled release CTC is highly desired because it leads to optimum cellulase activity through the wash.

EXAMPLE 3

The following multi-cycle washing machine test was carried out under the laundry conditions described in (5). The first treatment corresponds to a reference treatment where a level of cellulase of 10 CEVU/L is tested in absence CTC. The treatment 2 has a 5X higher level of cellulase and a CTC (described in 3). Treatment 3 is the same as treatment 2 except that it does not incorporate the CTC. Tensile strength loss and depilling benefits on cotton fabrics are monitored during the test.

| Treatment | Cellulase[1] level (CEVU/L) | CTC (2) | Depilling benefits[3] | TSL[4] |
|---|---|---|---|---|
| 1 (ref.) | 10 | no | 4.0 | 100 |
| 2 | 50 | yes | 1.6 | 107 |
| 3 | 50 | no | 1.4 | 150 |

[1]The cellulase is Carezyme ™ supplied by Novo Nordisk. Activity of the enzyme granulate is 1000 Cevu/g.
[2]Description of the CTC system: Peroxidase derived from *Coprinus cinereous* is supplied by Novo Nordisk. The concentration of peroxidase enzyme in the wash is 0.3 POXU/ml. The peroxidase enzyme is delivered in the form of a control release granulate (activity of the granulate is 30 KPOXU/g). The enhancer is PPT (phenothiazine-10-propionic acid). The concentration of PPT accelerator is 4 $\mu$M, concentration of PB1 in the wash is 35 ppm. Source of hydrogen peroxide is perborate mono-hydrate (PB1).
[3]Depilling benefits are determined by visual grading performed on cotton socks which have been pre-washed 10 times with detergent to create pills on the surface. Depilling is measured after 6 wash cycles. Depilling is measured on a scale from 1 (complete removal of pills) to 5 (high level of pills). A difference in pill grade which is $\geq 1$ is considered significant.
[4]Normalized tensile strength loss (TSL) is measured on standardised fabrics on an Instron instrument. In the above example, treatment 1 is the reference (100), the force necessary to break a piece of fabrics which has been washed 30 times (i.e. 30 wash cycles). Wash conditions are described in (5). A difference which is >10% is considered significant.
[5]Test conditions: The granular detergent is added via an granulette to a Miele washing machine. Detergent (6) concentration in the wash liquor is 8000 ppm. Wash conditions are as follows: water temperature is 40° C., water hardness is 8 grain/US gallon. Tests are run in the presence of a 3-kg load of clean fabrics (poly-ester, cotton, polycotton).
[6]The composition of the detergent used in the test is described in the table below. Non-ionic surfactant system used is a 2.7:1 mixture of Marlipal 24/50 (C24EO5) and C16/C18 glucose amide. HLB of these surfactant has been measured to be $\geq 10$. The pH of the detergent has been measured in the wash to be 9.5.

(1) The cellulase is Carezyme™ supplied by Novo Nordisk. Activity of the enzyme granulate is 1000 Cevu/g.

(2) Description of the CTC system: Peroxidase derived from Coprinus cinereous is supplied by Novo Nordisk. The concentration of peroxidase enzyme in the wash is 0.3 POXU/ml. The peroxidase enzyme is delivered in the form of a control release granulate (activity of the granulate is 30 KPOXU/g). The enhancer is PPT (phenothiazine-10-propionic acid). The concentration of PPT accelerator is 4 $\mu$M, concentration of PB1 in the wash is 35 ppm. Source of hydrogen peroxide is perborate mono-hydrate (PB1).

(3) Depilling benefits are determined by visual grading performed on cotton socks which have been pre-washed 10 times with detergent to create pills on the surface. Depilling is measured after 6 wash cycles. Depilling is measured on a scale from 1 (complete removal of pills) to 5 (high level of pills). A difference in pill grade which is $\geq 1$ is considered significant.

(4) Normalized tensile strength loss (TSL) is measured on standardised fabrics on an Instron instrument. In the above example, treatment 1 is the reference (100), the force necessary to break a piece of fabrics which has been washed 30 times (i.e. 30 wash cycles). Wash conditions are described in (5). A difference which is >10% is considered significant.

(5) Test conditions: The granular detergent is added via an granulette to a Miele washing machine. Detergent (6) concentration in the wash liquor is 8000 ppm. Wash conditions are as follows: water temperature is 40° C., water hardness is 8 grain/US gallon. Tests are run in the presence of a 3-kg load of clean fabrics (poly-ester, cotton, polycotton).

(6) The composition of the detergent used in the test is described in the table below. Non-ionic surfactant system used is a 2.7:1 mixture of Marlipal 24/50 (C24EO5) and C16/C18 glucose amide. HLB of these surfactant has been measured to be $\geq 10$. The pH of the detergent has been measured in the wash to be 9.5.

| | % by weight of the total formula |
|---|---|
| 45AS | 8.5 |
| 25E3S | 2.1 |
| 24E5 | 7.1 |
| C16/C18 glucose amide | 2.6 |
| Zeolite | 23.1 |
| Citrate | 7.7 |
| citric acid | 5.3 |
| Na-SKS-6 | 7.5 |
| Carbonate | 3.1 |
| Bicarbonate | 4.0 |
| Sulfate | 5.94 |
| Polyacrylate | 5.1 |
| CMC | 0.36 |
| PVNO/PVPVI | 0.19 |
| Protease | 0.87 |
| Lipase | 0.24 |
| Amylase | 0.8 |
| EDDS | 0.5 |
| Suds suppresser | 0.41 |
| Water and miscellaneous | Balance |

The test results shows that reference treatment 1 delivers a relatively low level of benefits. The benefit profile of treatment 1 is deficient compared to the high level of benefit seen in treatment 2 and 3. Treatment 3 however, shows a significant level of TSL compared to treatment 1 and 2. As a result, treatment 3 is deficient. Therefore, treatment 2 which contains the CTC is highly desired for benefits and because it is not deficient in the risk area.

EXAMPLE 4

Granular fabric cleaning compositions in accordance with the invention were prepared as follows:

| | I | II | III | IV |
|---|---|---|---|---|
| LAS | 22.0 | 22.0 | 22.0 | 22.0 |
| Phosphate | 30.0 | 23.0 | 23.0 | 23.0 |
| Carbonate/Bicarbonate** | 23.0 | 23.0 | 23.0 | 23.0 |
| Silicate | 14.0 | 14.0 | 14.0 | 14.0 |
| Zeolite A | — | 8.2 | 8.2 | 8.2 |

-continued

|  | I | II | III | IV |
|---|---|---|---|---|
| DETPMP | 0.4 | 0.4 | 0.4 | 0.4 |
| MA/AA | 1.0 | 0.5 | 1.0 | 1.0 |
| Sodium Sulfate | 5.5 | 5.5 | 5.5 | 5.5 |
| * Protease | 0.01 | 0.02 | 0.01 | 0.005 |
| * Lipolytic enzyme(s) | 0.005 | 0.01 | — | 0.01 |
| * Cellulase (1000 CEVU/g) | 0.3 | 0.5 | 0.8 | 0.3 |
| * Amylase | 0.01 | — | 0.01 | 0.006 |
| * Pectinase | 0.02 | 0.02 | 0.02 | — |
| * Xylanase | 0.01 |  |  |  |
| CTC | + | + | + | + |
| Water/minors | Up to 100% | | | |

*The level of enzyme(s) is by weight of "pure" enzyme
**to control pH

EXAMPLE 5

Granular fabric cleaning compositions in accordance with the invention were prepared as follows:

|  | I | II | III | IV |
|---|---|---|---|---|
| LAS | 12.0 | 12.0 | 12.0 | 12.0 |
| Zeolite A | 26.0 | 26.0 | 26.0 | 26.0 |
| SS | 4.0 | 4.0 | 4.0 | 4.0 |
| SAS | 5.0 | 5.0 | 5.0 | 5.0 |
| Citrate/Citric acid** | 10.0 | 10.0 | 10.0 | 10.0 |
| Sodium Sulfate | 20.0 | 20.0 | 20.0 | 30.0 |
| MA/AA | 1.5 | 1.5 | — | — |
| AA | — | — | 1.0 | — |
| * Protease | 0.06 | 0.03 | 0.02 | 0.08 |
| * Lipolytic enzyme(s) | — | 0.01 | 0.005 | 0.01 |
| * Cellulase | 0.5 | 0.8 | 0.4 | 0.8 |
| * Amylase | — | 0.01 | 0.01 | 0.005 |
| * Pectinase | — | — | 0.02 | 0.01 |
| * Xylanase | — | — | 0.02 | — |
| CTC | + | + | + | + |
| Water/minors | Up to 100% | | | |

*The level of enzyme(s) is by weight of "pure" enzyme
**to control pH

EXAMPLE 6

Granular fabric cleaning compositions in accordance with the invention which are especially useful in the laundering of coloured fabrics were prepared as follows:

|  | A | B | C | D |
|---|---|---|---|---|
| LAS | 11.4 | 10.7 | — | 11 |
| TAS | 1.8 | 2.4 | — | 5 |
| TFAA | — | — | 4.0 | — |
| 45AS | 3.0 | 3.1 | 10.0 | — |
| 45E7 | 4.0 | 4.0 | — | 6 |
| 25E3S | — | — | 3.0 | — |
| 68E11 | 1.8 | 1.8 | — | — |
| 25E5 | 2.0 | — | 8.0 | — |
| Citrate/Citric acid** | 17.0 | 17.5 | 10.0 | 21 |
| Carbonate | — | — | 10 | 5 |
| Zeolite A | 32.5 | 32.1 | 25.0 | 32 |
| Na-SKS-6 | — | — | 9.0 | — |
| MA/AA | 5.0 | 5.0 | 5.0 | 4.0 |
| DETPMP | 1.0 | 0.2 | 0.8 | 0.2 |
| * Protease | 0.02 | 0.02 | 0.01 | 0.02 |
| * Lipolytic enzyme(s) | 0.03 | 0.04 | 0.005 | 0.04 |
| * Amylase | — | 0.03 | 0.005 | 0.01 |
| * Pectinase | — | — | 0.01 | — |
| * Cellulase | 0.8 | 0.8 | 0.8 | 2.5 |
| * Xylanase | — | — | 0.02 | — |
| Silicate | 2.0 | 2.5 | — | 2.0 |
| Sulphate | 3.5 | 5.2 | 3.0 | 5.0 |
| PVP | 0.3 | 0.5 | — | 0.3 |
| Poly (4-vinylpyridine)-N-oxide/copolymer of vinyl-imidazole and vinyl-pyrrolidone | — | — | 0.2 | — |
| CTC | + | + | + | CTCI |
| Water/minors | Up to 100% | | | |

*The level of enzyme(s) is by weight of "pure" enzyme
**to control pH

EXAMPLE 7

Granular fabric cleaning compositions in accordance with the invention were prepared as follows:

| LAS | 6.5 | 8.0 |
|---|---|---|
| Sulfate | 15.0 | 18.0 |
| Zeolite A | 30.0 | 25.0 |
| Sodium nitrilotriacetate | 5.0 | 5.0 |
| PVP | 0.5 | 0.7 |
| Boric acid | 4.0 | — |
| Silicate | 5.0 | 5.0 |
| Carbonate | 15.0 | 15.0 |
| * Protease | 0.06 | 0.02 |
| * Lipolytic enzyme(s) | 0.01 | 0.01 |
| * Amylase | 0.01 | 0.01 |
| * Cellulase (1000 CEVU/g) | 0.6 | 0.8 |
| CTC | + | + |
| Water/minors | Up to 100% | |

*The level of enzyme(s) is by weight of "pure" enzyme

EXAMPLE 8

Compact granular fabric cleaning compositions in accordance with the invention was prepared as follows:

| 45AS | 8.0 | 8.0 |
|---|---|---|
| 25E3S | 2.0 | 2.0 |
| 25E5 | 3.0 | 3.0 |
| 25E3 | 3.0 | 3.0 |
| TFAA | 2.5 | 2.5 |
| Zeolite A | 27.0 | 20 |
| NaSKS-6 | 12.0 | 10 |
| Citric acid/Citrate** | 10.0 | 10 |
| Carbonate | 7.0 | 5 |
| MA/AA | 5.0 | 4 |
| CMC | 0.4 | 0.4 |
| Poly (4-vinylpyridine)-N-oxide/copolymer of vinylimidazole and vinylpyrrolidone | 0.2 | 0.2 |
| Crosslinked poly(4-vinylpyridine)-N-oxide | — | 0.2 |
| * Protease | 0.05 | 0.05 |
| * Lipolytic enzyme(s) | 0.005 | 0.005 |
| * Cellulase | 0.5 | 0.5 |
| * Amylase | 0.01 | 0.01 |
| * Xylanase | 0.05 | 0.05 |
| EDDS | 0.3 | 0.3 |
| Granular suds suppressor | 3.5 | 3.5 |
| CTC | + | + |
| Water/minors | Up to 100% | |

*The level of enzyme(s) is by weight of "pure" enzyme
**to control pH

EXAMPLE 9

A granular fabric cleaning compositions in accordance with the invention which provide "softening through the wash" capability were prepared as follows:

| | | | |
|---|---|---|---|
| 45AS | — | 10.0 | — |
| LAS | 7.6 | — | 7.6 |
| 68AS | 1.3 | — | 1.3 |
| 45E7 | 4.0 | — | 2.0 |
| 25E3 | — | 5.0 | 3.0 |
| Coco-alkyl-dimethyl hydroxy-ethyl ammonium chloride | 1.4 | 1.0 | — |
| Choline ester | — | — | 1.5 |
| Citrate/Citric acid** | 8.0 | 15.0 | 12 |
| Na-SKS-6 | — | 11.0 | 3 |
| Zeolite A | 15.0 | 15.0 | 15 |
| MA/AA | 4.0 | 4.0 | 4 |
| DETPMP | 0.4 | 0.4 | 0.4 |
| Smectite clay | 10.0 | 10.0 | 10 |
| HMWPEO | — | 0.1 | 0.2 |
| * Protease | 0.02 | 0.01 | 0.01 |
| * Lipolytic enzyme(s) | 0.02 | 0.01 | 0.02 |
| * Amylase | 0.03 | 0.005 | 0.03 |
| * Cellulase (1000 CEVU/g) | 0.5 | 0.5 | 0.6 |
| Silicate | 3.0 | 5.0 | 3.0 |
| Carbonate | 10.0 | 10.0 | 8.0 |
| Granular suds suppressor | 1.0 | 4.0 | 2.0 |
| CMC | 0.2 | 0.1 | 0.1 |
| CTC | + | + | + |
| Water/minors | | Up to 100% | |

*The level of enzyme(s) is by weight of "pure" enzyme
**to control pH

EXAMPLE 10

Heavy duty liquid fabric cleaning compositions suitable for use in the pretreatment of stained fabrics, and for use in a machine laundering method, in accordance with the invention were prepared as follows:

| | I | II | III | IV | V |
|---|---|---|---|---|---|
| 24AS | 20.0 | 20.0 | 20.0 | 20.0 | 20.0 |
| SS | 5.0 | 5.0 | 5.0 | 5.0 | 5.0 |
| Citrate | 1.0 | 1.0 | 1.0 | 1.0 | 1.0 |
| $12E_3$ | 13.0 | 13.0 | 13.0 | 13.0 | 13.0 |
| Monethanolamine | 2.5 | 2.5 | 2.5 | 2.5 | 2.5 |
| * Protease | 0.005 | 0.03 | 0.02 | 0.04 | 0.01 |
| * Lipolytic enzyme(s) | 0.002 | 0.01 | 0.02 | — | 0.004 |
| * Amylase | 0.005 | 0.005 | — | — | 0.004 |
| * Cellulase (1000 cevu/g | 0.5 | 0.5– | 0.6 | 0.6 | 0.8 |
| * Pectinase | — | 0.02 | — | — | 0.02 |
| * Xylanase | — | — | — | — | 0.03 |
| CTC | + | + | + | + | + |
| Water/propylene glycol/ethanol (100:1:1) | | | | | |

*The level of enzyme(s) is by weight of "pure" enzyme

EXAMPLE 11

Heavy duty liquid fabric cleaning compositions in accordance with the invention were prepared as follows:

| | I | II | III | IV |
|---|---|---|---|---|
| LAS acid form | — | — | 25.0 | — |
| $C_{12–14}$ alkenyl succinic acid | 3.0 | 8.0 | 10.0 | — |
| Citric acid | 10.0 | 15.0 | 2.0 | 2.0 |
| 25AS acid form | 8.0 | 8.0 | — | 15.0 |
| 25AE2S acid form | — | 3.0 | — | 4.0 |
| 25AE7 | — | 8.0 | — | 6.0 |
| 25AE3 | 8.0 | — | — | — |
| CFAA | — | — | — | 6.0 |
| DETPMP | 0.2 | — | 1.0 | 1.0 |
| Fatty acid | — | — | — | 10.0 |
| Oleic acid | 1.8 | — | 1.0 | — |
| Ethanol | 4.0 | 4.0 | 6.0 | 2.0 |
| Propanediol | 2.0 | 2.0 | 6.0 | 10.0 |
| * Protease | 0.02 | 0.02 | 0.02 | 0.01 |
| * Lipolytic enzyme(s) | 0.01 | 0.005 | — | 0.01 |
| * Amylase | 0.005 | 0.01 | — | 0.01 |
| * Cellulase (1000 cevu/ml) | 0.5 | 0.4 | 0.4 | 0.5 |
| * Pectinase | 0.02 | — | — | — |
| * Xylanase | 0.05 | — | — | — |
| Coco-alkyl dimethyl hydroxy ethyl ammonium chloride | — | — | 3.0 | — |
| Smectite clay | — | — | 5.0 | — |
| PVP | 1.0 | 2.0 | — | — |
| CTC | + | + | + | + |
| NaOH | | Up to pH 7.5 | | |
| Waters/minors | | Up to 100% | | |

*The level of enzyme(s) is by weight of "pure" enzyme

| | Additive Product | |
|---|---|---|
| | I | II |
| Cellulase | 20 | 25 |
| POD | 20 | 15 |
| Enhancer CPPT | 5 | 8 |
| Perborate | 20 | — |
| Percarbonate | — | 20 |
| Citric acid | 5 | 5 |
| Filler | Up to 100% | |

EXAMPLE 12

What is claimed is:

1. A detergent composition comprising
   (i) cellulase;
   (ii) cellulase terminator composition comprising
      a) a peroxidase;
      b) an enhancer, wherein the enhancer is incorporated into a release agent;
      c) a source of hydrogen peroxide characterized in that the activity of the cellulase is controlled in such a way that the activity of the cellulase is more than 90% within 5 minutes from the start of the wash cycle, the cellulase activity is less than 50% within 5 to 10 minutes from the start of the wash cycle and that less than 10% of residual cellulase activity is reached after 15 minutes in the wash cycle.

2. A detergent composition according to claim 1, wherein one or more of the compounds a) and c) is incorporated into a release agent.

3. A detergent composition according to claim 1 wherein said cellulase is 43 kD endoglucanase derived from Humicola insolens, DSM 1800.

4. A detergent composition according to claims 1 wherein the source of hydrogen peroxide is a peroxygen bleach including percarbonates and perborates.

5. A detergent composition according to claim 1 wherein said enhancer is 10-phenothiazinepropionic acid (PPT), 10-ethylphenothiazine-4-carboxylic acid (EPC), 10-phenoxazinepropionic acid (POP).

6. A detergent composition according to claim 1 further comprising anionic surfactants and nonionic surfactants.

7. A detergent composition according to claim 6 wherein the weight ratio of anionic to nonionic is between 10:1 to 1:2.

8. A detergent composition according to claim 1 wherein the pH is between 8 to 10.

9. A detergent composition according to claim 1 further comprising a protease.

10. A detergent composition according to claim 1 further comprising a clay.

11. A detergent composition according to claim 1 further comprising a cationic surfactant.

12. A detergent composition according to claim 1 further comprising a protease.

13. A detergent composition according to claim 1 which is in the form of a liquid, granular, gel, paste or bar.

14. A detergent additive which comprises the detergent composition of claim 1.

15. A detergent composition comprising
(i) cellulase;
(ii) cellulase terminator composition comprising
   a) a peroxidase;
   b) an enhancer wherein the enhancer is incorporated into a release agent;
   c) a source of hydrogen peroxide characterized in that the activity of the cellulase is controlled in such a way that the activity of the cellulase is more than 90% within 5 minutes from the start of the wash cycle, the cellulase activity is less than 50% within 5 to 10 minutes from the start of the wash cycle and that less than 10% of residual cellulase activity is reached after 15 minutes in the wash cycle; and
(iii) a surfactant system comprising sodium linear $C_{12}$ alkylbenzenesulfonate.

* * * * *